(12) United States Patent
Mueller et al.

(10) Patent No.: US 6,949,243 B1
(45) Date of Patent: Sep. 27, 2005

(54) METHODS OF INHIBITING METASTASIS

(75) Inventors: Anja Mueller, Palo Alto, CA (US); Albert Zlotnik, Palo Alto, CA (US)

(73) Assignee: Schering Corporation, Kenilworth, NJ (US)

( * ) Notice: Subject to any disclaimer, the term of this patent is extended or adjusted under 35 U.S.C. 154(b) by 0 days.

(21) Appl. No.: 09/721,613

(22) Filed: Nov. 22, 2000

Related U.S. Application Data

(60) Provisional application No. 60/225,562, filed on Aug. 14, 2000, provisional application No. 60/167,519, filed on Nov. 24, 1999.

(51) Int. Cl.[7] ............................................. A61K 39/395
(52) U.S. Cl. ................................. 424/130.1; 424/138.1
(58) Field of Search ........................... 424/85.1, 130.1, 424/143.1, 145.1; 514/2

(56) References Cited

FOREIGN PATENT DOCUMENTS

| EP | EP 0897980 A2 | 2/1999 |
|---|---|---|
| WO | WO 96/06169 | 2/1996 |
| WO | WO 98/11218 | 3/1998 |
| WO | WO 99/47158 A2 * | 9/1999 |
| WO | WO 00/38713 | 7/2000 |
| WO | WO 00/46248 | 8/2000 |

OTHER PUBLICATIONS

Negus RP et al World J Urol 1996;14(3):157-65.*
Wang et al J. Immunol Meth 1998;220:1-17.*
Mohle et al (Blood Jun. 15, 1998;91(21):4523-4530).*
Loetscher et al (J. Biol. Chem. Aug. 28, 1998:273(35): 22279-22283).*
The On-line Medical Dictionary is ©Academic Medical Publishing & The CancerWEB Project 1997-2002 http://medical-dictionary.com/ Nov. 18, 1997.*
Fujisawa N et al. (Melanoma Res Apr. 9, 1999(2):105-114).*
Freshney (Culture of Animal Cells, A Manual of Basic Technique, Alan R. Liss, Inc., 1983, New York, p4).*
Dermer (Bio/Technology, 1994, 12:320).*
A. Aiuti, et al., *Journal of Experimental Medicine*, 185:111-120, 1997. "The Chemokine SDF-1 Is a Chemoattractant for Human CD34[+] Hematopoietic Progenitor Cells and Provides a New Mechanism to Explain the Mobilization of CD34[+] Progenitors to Peripheral Blood".
Kevin Beaumont and Paul Negulescu, *Nature biotechnology*, 17:1060-1108, 1999. "Chipping Away at GPCR Function".
Christopher Bieri, et al., *Nature Biotechnology*, 17:1105-1108, Nov. 1999. "Micropatterned immobilization of a G protein-coupled receptor and direct detection of G protein activation".
M. Birkenbach, et al., *Genbank*, Accession No. NM_001838, Oct. 31, 2000 "*Homo sapiens* chemokine (C-C motif) receptor 7 (CCR7), mRNA."

Barak A. Cohen, et al., 95:14272-14277, 1998. "An artificial cell-cycle inhibitor isolated from a combinatorial library".
B. Federsppiel, et al., *Genbank*, Accession No. NM_003467, Nov. 1, 2000. "Homo sapiens chemokine (C-X-C motif), receptor 4 (fusin) (CXCR4), mRNA.".
Jorg Kleeff, et al., *International Journal of Cancer*, 81:650-657, 1999. "Detection and Localization of MIP-3alpha/LARC/EXODUS, a m,acrophage proinlammatory chemokine, and its CCR6 receptor in human pancreatic cancer".
Mikhail G. Kolonin and Russell L Finley, Jr., *Proceedings of the National Academy of Sciences*, 95:14266-14271, 1998. "Targeting cyclin-dependent kinases in *Drosophila* with peptide aptamers".
Simon F. Lacey, et al. *Proceedings of the National Academy of Sciences*, 94:9842-9847 1997. "The CXC chemokine stromal cell-derived factor 1 is not responsible for CD8[+] T cell suppression of syncytia-inducing strains of HIV-1".
A. Marchese, et al., *Genbank*, Accession No. U13667, Apr. 1, 1995. "Human G protien-coupled receptor (GPR2) gene, partial cds".
M. Marra, et al., *Genbank*, Accession No. AA620142, Oct. 9, 1997. "vo63a06.r1 Soares_mammary_gland_NbMMG Mus musculus cDNA clone IMAGE:1054546 5' similar to gb:L12030 Mus musculus cytokine (MOUSE);, mNRNA sequence gi|2524018|gb|AA620142.1|AA620142 [2524018]".
B. Moser, *Gennbank,* Accession No. X71635, Feb. 15, 1994. "H.sapiens mRNA for neuropedtide Y-like receptor."
D. Rossi, et al., *GenBank*, Accession No. U77180, Jan. 23, 1997. "Human macrophage inflammatory protein 3 beta (MIP-3beta) mRNA, complete cds."
Thomas J. Schall and Kevin B. Bacon, *Current Opinion in Immunology*, 6:865-873, 1994. "Chemokines, leukocyte trafficking, and inflammation".
V.L Schweickart, *Genbank* Accession No. L_31581, Aug. 10, 1995. "Human G protein-coupled receptor (EBI 1) mRNA, complete cds."
Robert Strausberg, *Genbank* Accession No. AI670734, May 18, 1999. "SW:GPR2_Human P46092 Probable G Protein-Coupled Receptor GPR2."
K. Tashiro, et al. *GenBank*, Accession No. L12030, Sept. 3, 1993. "Mus musculus cytokine (SDF-1-beta) mRNA, complete cds."
Sara J. Youngs, et al., *International Journal of Cancer*, 71: 257-266, 1997. "Chemokines Induce Migrational Responses in Human Breast Carcinoma Cell Lines".
Muller et al., Involvement of chemokine receptors in breast cancer metastasis. Nature. Mar. 1, 2001:410(6824):50-56.

* cited by examiner

*Primary Examiner*—Jeffrey Siew
*Assistant Examiner*—C. Yaen
(74) *Attorney, Agent, or Firm*—Thomas Triolo

(57) ABSTRACT

Methods of inhibiting metastasis or maintenance of various cancers are provided. In particular, the method makes use of fact that certain trafficking of cancers depend upon identified proteins, which serve as markers. Additional methods of screening are also provided.

10 Claims, No Drawings

METHODS OF INHIBITING METASTASIS

The present filing is a U.S. utility patent application claiming priority to U.S. Ser. No. 60/225,562, filed Aug. 14, 2000, and U.S. Ser. No. 60/167,519, filed Nov. 24, 1999, each of which is incorporated herein by reference.

FIELD OF THE INVENTION

The invention relates generally to methods of inhibiting metastasis of various cancers. It also provides methods for screening for various proteins which will exhibit similar biological activity.

BACKGROUND

Even if a primary cancer is completely eliminated, a malignant tumor will often be metastatic. The formation of metastases of malignant tumors, initiated from a primary tumor at more or less remote locations of the body, is one of the most serious effects of cancer and one for which a satisfactory treatment protocol is currently unavailable. Cancer tumor metastasis is responsible for most therapeutic failures when the disease is treated, as patients succumb to the multiple tumor growth. Important tumors include, e.g., carcinomas, including breast, head and neck, lung, colon, prostate, and melanomas. See, e.g., Bertino, et al. (eds. 1996) *Encyclopedia of Cancer* Academic Press; Devita, et al. (eds. 1997) *Cancer: Principles & Practice of Oncology* Lippincott, Williams and Wilkins; Devita (1997) *Principles and Practice of Oncology* Lippincott Williams and Wilkins; Cavalli, et al. (1996) *Textbook of Medical Oncology* Dunitz Martin Ltd; Horwich (ed. 1995) *Oncology: A Multidisciplinary Textbook* Lippincott-Raven; Peckham, et al. (eds. 1995) *Oxford Textbook of Oncology* Oxford Univ. Press; Mendelsohn, et al. (1995) *The Molecular Basis of Cancer* Saunders, Philadelphia; and McArdle (1990) *Surgical Oncology: Current Concepts and Practice* Butterworth-Heinemann.

The extent to which metastasis occurs varies with the individual type of tumor. Melanoma, breast cancer, lung cancer, colon cancer, and prostate cancer are among the types of cancer that are prone to metastasize. When metastasis takes place, the metastases can form at a variety of sites in the body, with lymph nodes, lungs, liver, brain and bone marrow being the more common sites.

The currently available methods of cancer therapy such as surgical therapy, radiotherapy, chemotherapy, and immuno-biological methods have either been of limited success in preventing metastasis or these methods give rise to serious and undesirable side effects.

In many clinically diagnosed solid tumors (in which the tumor is a localized growth) surgical removal is considered the prime means of treatment. However, many times after surgery and after some delay period, the original tumor is observed to have metastasized so that secondary sites of cancer invasion have spread throughout the body and the patient subsequently dies of the secondary cancer growth. Reports indicate that in individuals with resectable tumors, primary tumor growth or local recurrence is not often the cause of death. Instead, at present, nearly 40% of cancer victims with operable tumors ultimately succumb to metastatic disease following surgery.

Although chemotherapy is widely used in the treatment of cancer, it is a systemic treatment based usually on the prevention of cell proliferation. Accordingly, chemotherapy is a non-specific treatment modality affecting all proliferating cells, including normal cells, leading to undesirable and often serious side effects, e.g., immunosuppression, pancytopenia (growth inhibition of bone marrow cells with anemia, thrombocytopenia, and leukopenia), diarrhea, nausea and alopecia (hair loss).

Often, the existing systemic treatments have proven to have little effect on macrometastases already residing in remote organs (lung, liver, bone marrow, or brain). Patients are often killed with metastatic cancers provoked by metastasis of cancer cells. A method for effectively suppressing the metastasis of the cancer cells has not been established, and a medicine having a cancer cell metastasis suppressing effect has not yet been made commercially available.

Thus, the need exists for methods of inhibiting tumor metastasis. In particular, methods which inhibit metastasis without causing serious side effects are much desired.

SUMMARY OF THE INVENTION

The present invention is based, upon the hypothesis that signaling through chemokine receptors may be an important attractant mechanism for metastasizing cancer cells. Data supporting such model have been collected. Alternatively, the specific expression by tumor cells of chemokine receptors may allow for prevention of progression of growth, or even shrinkage, e.g., by chemokine receptor targeted therapeutic agents, alone or in combination with other anticancer therapies.

The present invention provides methods of inhibiting metastasis of a cell, e.g., a tumor cell, the method comprising blocking signaling of a chemokine receptor on the cell. Preferably, the metastasis is organ specific, e.g., to the lymph node, bone marrow, or skin, or the cell is a carcinoma cell, including a breast, head and neck, melanoma, or prostate. In other embodiments, the chemokine receptor is CCR7, CXCR4, or CCR10. The blocking of signaling can be with an antibody against the chemokine receptor, a mutein antagonist of the ligand, or a drug which inhibits signaling of the chemokine receptor, e.g., pertussis toxin. Thus, e.g., when the chemokine receptor is CCR7, the blocking may be with: an antibody against FSEC, CKβ9, or CKβ11; or an antagonist mutein of FSEC, CKβ9, or CKβ11; when the chemokine receptor is CXCR4, the blocking may be with: an antibody against SDF-1; or an antagonist mutein of SDF-1; and when the chemokine receptor is GPR2, the blocking may be with: an antibody against CTACK or Vic; or an antagonist mutein of CTACK or Vic. Use of toxic conjugates to target drugs to chemokine receptor expressing tumors may also be effected.

Typically, the method is combined with another treatment for cancer, e.g., chemotherapy, radiation therapy, immunotherapy, or surgery. Often the method is applied after such treatment, but it may be prophylactic. And the treatment may be directly to affect primary tumor progression or growth.

Alternatively, the invention provides methods of screening for chemokine receptors on metastatic or primary tumor cells, comprising identifying which chemokine receptors are expressed on the cell. The identifying may be by, e.g., antibody labeling, ligand testing, or PCR analysis; or may be useful in determination of therapeutic strategy. The labeling may allow for directed cell killing, e.g., with toxic conjugates, or with absorption reagents allowing for absorption of energy or binding of toxic compounds.

Yet another embodiment includes a composition comprising an anti-tumor agent and a chemokine receptor antagonist or label. In such embodiments, the antagonist or label may be an antibody against FSEC, CKβ9, or CKβ11; an antagonist mutein of FSEC, CKβ9, or CKβ11; an antibody against SDF-1; an antagonist mutein of SDF-1; an antibody against CTACK or Vic; an antagonist mutein of CTACK or Vic; an antibody against the chemokine receptor; or a drug which inhibits signaling of the chemokine receptor including pertussis toxin. Methods using such compositions are provided, e.g., methods of treating a cancer in an animal, metastasizing or primary, comprising administering to the animal an effective amount of the composition.

DETAILED DESCRIPTION OF THE INVENTION

Outline
I. General
II. Chemokine Agonists and Antagonists
   A. Ligands and Variants
   B. Antibodies
   C. Other Molecules
III. Immunoassays
IV. Uses I. General The invention is based, in part, on the surprising discovery of a correlation suggesting that chemokines may be important mediators of cancer metastasis. In particular, metastatic tumors have been analyzed for chemokine receptor expression. Various primary tumors have also been evaluated for chemokine receptor expression, and the identification of the receptors as markers may have therapeutic value.

Organ specific metastatic tumors appear to express specific chemokine receptors. These chemokine receptors appear to correspond to the ligand expression of the common metastatic target organs of the various cancers evaluated. Moreover, in evaluation of the primary tumors, the chemokine receptor expression patterns also match the ligands expressed by the metastatic target organs. Thus, those metastatic tumor cells likely were directed to the target organ, in part, by the chemokines expressed by those target organs. If so, then metastasis will be responsive to blocking of chemokine mediated trafficking and organ targeting.

In addition, identification of various chemokine receptors as markers for specific tumor types provides the possibility of using them as markers to target appropriate therapeutics. Toxic conjugates, specific localization of radiation or energy absorbents, or means to attract anticancer drugs to the sites of primary tumors will be useful.

The chemokines are a sub-family of chemoattractant cytokines that were classically characterized by their ability to mediate leukocyte trafficking or migration by binding to specific G-protein linked seven transmembrane spanning receptors, or GPCRs. Chemokines are divided into four groups based on the primary sequence of the first two cysteines: the CXC, CC, C, and CX3C families.

The chemokine receptors are typically members of the superfamily of G-protein coupled (or linked) receptors (GPCR, or GPLR). As a class, these receptors are integral membrane proteins characterized by amino acid sequences which contain seven hydrophobic domains. See, e.g., Ruffolo and Hollinger (eds. 1995) *G-Protein Coupled Transmembrane Signaling Mechanisms* CRC Press, Boca Raton, Fla.; Watson and Arkinstall (1994) *The G-Protein Linked Receptor FactsBook* Academic Press, San Diego, Calif.; Peroutka (ed. 1994) *G Protein-Coupled Receptors* CRC Press, Boca Raton, Fla.; Housley and Milligan (1990) *G-Proteins as Mediators of Cellular Signaling Processes* Wiley and Sons, New York, N.Y.; and Dohlman, et al. (1991) *Ann. Rev. Biochem.* 60:653–688. These hydrophobic domains are predicted to represent transmembrane spanning regions of the proteins. These GPCRs are found in a wide range of organisms and are typically involved in the transmission of signals to the interior of the cell, e.g., through interaction, e.g., with heterotrimeric G-proteins. They respond to a wide and diverse range of agents including lipid analogs, amino acid derivatives, small peptides, and other molecules. The chemokine ligands for the receptors typically initiate a calcium flux upon binding to the receptor, and the calcium flux is typically pertussis toxin sensitive. Besides chemoattractant properties, chemokines have been shown to induce other biological responses, e.g., modulation of second messenger levels such as $Ca^{++}$; inositol phosphate pool changes (see, e.g., Berridge (1993) *Nature* 361:315–325 or Billah and Anthes (1990) *Biochem. J.* 269:281–291); cellular morphology modification responses; phosphoinositide lipid turnover; possible antiviral responses; and others.

The best known biological functions of chemokine molecules relate to chemoattraction of leukocytes. It would not be peculiar that trafficking of other cell types, e.g., primary tumor cells expressing those chemokine receptors, would likewise be directed by chemokines to specific organs. See, e.g., Youngs, et al. (1997) *Int. J. Cancer* 71:257–266; and Kleeff, et al. (1999) *Int. J. Cancer* 81:650–657.

A significant panel of tumor cell lines of various types were collected, most available from the ATCC. These included breast carcinoma, head and neck, melanoma, and prostate cancer cell lines. The cell lines were analyzed for expression of a number of chemokine receptors by quantitative PCR techniques. By this analysis, chemokine receptor expression was generally very low, with the exception of the CCR7 (see GenBank L31581), the CXCR4 (see GenBank X71635), and the GPR2 (see GenBank U13667; also designated CCR10) receptors. The breast cancer lines generally expressed the CCR7, CXCR4, and GPR2 receptors. The head and neck tumor lines generally expressed the CCR7 receptor. The melanoma cell lines generally expressed the CCR7, CXCR4, and GPR2 receptors. In summary, the CCR7 receptor was expressed by the breast cancer, head and neck, and melanoma cell lines; the CXCR4 receptor was expressed by the breast cancer and melanoma cell lines; and the GPR2 receptor was expressed by breast cancer and melanoma cell lines. The prostate carcinoma lines expressed CCR7, CXCR4, CCR8, and STRL33; the breast cancer cell lines also expressed CCR8 and STRL33.

Each of these receptors has been matched with chemokine ligands. The chemokines MIP-3β (GenBank U77180; see Coleman, et al. WO9622374A1 (FSEC)) and CKβ9 (GenBank W17274; see Adams and Li WO9606169A1) are the ligands for the CCR7 receptor. Both of these chemokines are expressed by lymph nodes, which is probably why all three tumor cell types often metastasize to the lymph node. The chemokine SDF-1 (stromal cell derived factor 1; GenBank L12030 and AA620142; see Lacey, et al. (1997) *Proc. Nat'l Acad. Sci. USA* 94:9842–9847, and Aiuti, et al. (1997) *J. Exp. Med.* 185:111–120) is the ligand for the CXCR4 receptor. This chemokine is expressed by bone marrow stromal cells, which is probably why breast cancers often metastasize to the bone marrow. The CXCR4 has also been implicated in liver, lung, and lymph node metastasis because SDF-1 is also expressed by stromal cells of these organs. The chemokines CTACK (CCL27; GenBank U13667; see Hedrick, et al. WO9823750A2) and Vic (CCL28; GenBank R38459; see Hedrick, et al. WO9823750A2) are the ligands for the GPR2 receptor. These chemokines are expressed in the skin, which probably explains why melanomas metastasize to the skin.

Besides metastatic effects, the SDF-1 and CTACK may have important contributions to primary tumor formation or progression of growth and/or angiogenesis. This occurs with certain other tumors, and there is reason to believe this may be true in melanomas.

In a similar fashion for other types of cancers, chemokine receptors which are expressed by primary tumors seem generally to have ligands which are expressed in the target organs for frequent metastasis. This method may be used to confirm the hypothesis in other tumor cell types. Looking at primary tumors, analysis of chemokine receptors will indicate what chemokines those cells are likely to be chemoattracted by. Thus, blockage of metastasis of those primary tumors should be mediated by blockage of such chemoattraction. The blockage may be effected by ligand antagonists or receptor antagonists. Such may be ligand mutein antagonists, antibody antagonists to ligand or receptor, or drugs, e.g., small molecules, which block chemoattraction.

The most common other primary tumor types include, e.g., prostate cancer, gastrointestinal (including colon) cancer, and lung cancer. Prostate cancers tend to metastasize to lymph nodes and bone marrow, suggesting that the CCR7 and CXCR4 receptors are involved, mediated by their respective ligands. Gastrointestinal cancers tend to metastasize to lymph nodes and liver, suggesting that the CCR7 and CCR6 receptors are involved. The ligand for the CCR6 receptor is the chemokine MIP-3α. Lung cancers tend to metastasize to the lymph nodes, bone marrow, and brain, suggesting that the CCR7, CXCR4, and V28 chemokine receptors are involved, mediated by their respective chemokine ligands. The ligand for the V28 receptor is the chemokine CX3C (neurotactin). The present invention teaches what antagonists will have effects on certain types of primary tumor metastasis or progression.

Conversely, chemokines expressed by target tissues for metastasis are likely mediators of chemoattraction. Thus, metastasis may be blocked by inhibiting the chemoattraction or tumor progression may be targeted, e.g., at the chemokine receptors as markers. It is likely that metastasis to the lymph nodes is mediated by the CCR7 and CXCR4 receptors, to the bone marrow by the CXCR4 receptor, to the skin by the GPR2 receptor, to the liver by the CXCR4 CCR6 receptors, to the brain by the V28 receptor, and to the lung by the CXCR4 receptor. Likewise, the present invention teaches what antagonists will have effects on metastasis to specific organs or markers for primary tumors. And the specific expression of chemokine receptors on primary tumors allow for specific targeting of therapeutic agents to those sites.

In either case, mouse models will be useful in confirmation of the teachings. The testing of other primary tumor types or target organs for receptor/chemokine pairings responsible for the metastasis or primary tumor progression, e.g., growth and/or angiogenesis, will be continued, e.g., other types of carcinomas, sarcomas, etc. Primary tumor progression may be also targeted.

II. Chemokine Agonists and Antagonists

Chemokine ligands for the receptors have been described. Various agonists and antagonists of the natural ligands or receptors can be produced. Receptor binding assays can be developed. See, e.g., Bieri, et al. (1999) *Nature Biotechnology* 17:1105–1108, and accompanying note on page 1060. Calcium flux assays may be developed to screen for compounds possessing antagonist activity. Migration assays may take advantage of the movement of cells through pores in membranes, which can form the basis of antagonist assays. Chemotaxis may be measured thereby. Alternatively, chemokinetic assays may be developed, which measure the induction of kinetic movement, not necessarily relative to a gradient, per se.

A. Chemokine Ligands and Variants

Chemokine agonists will exhibit some or all of the signaling functions of the chemokine, e.g., binding, inducing a Ca++flux, and chemoattracting appropriate receptor bearing cells. Conversely, antagonists will block the signaling and/or effector biology. Various mammalian chemokine sequences may be evaluated to determine what residues are conserved across species, suggesting what residues may be changed without dramatic effects on biological activity. Alternatively, conservative substitutions in certain regions of the molecule are somewhat more likely to maintain receptor binding activity, while other regions will more likely affect signal transduction. Standard methods for screening mutant or variant chemokine polypeptides will determine what sequences will be useful therapeutic antagonists.

In addition, certain nucleic acid expression methods may be applied. For example, in certain contexts, it may be useful to transfect cells with various nucleic acids which will be expressed, as appropriate. Various promoters may be operably linked to the gene, thereby allowing for regulated expression, e.g., suppression.

Antagonist activity may be tested or screened for using well known methods. Tests for ability to antagonize chemokine binding, calcium flux, or chemoattractant activity can be developed. Various ligand homologs can be created which retain receptor binding capacity, but lack signaling capability, thus serving as competitive binding molecules. Small molecules may also be screened for ability to antagonize chemokine function, e.g., chemoattraction, receptor binding, Ca++ flux, and other effects mediated by chemokine. See generally Gilman, et al. (eds. 1990) *Goodman and Gilman's: The Pharmacological Bases of Therapeutics*, 8th Ed., Pergamon Press; *Remington's Pharmaceutical Sciences*, 17th ed. (1990), Mack Publishing Co., Easton, Pa., each of which is incorporated herein by reference. Agonists or antibodies may function as means to target, e.g., for labeling or specific localization, primary tumor types.

B. Antibodies

The present invention provides for the use of an antibody or binding composition which specifically binds to chemokine or receptor, preferably mammalian, e.g., primate, human, cat, dog, rat, or mouse, and neutralizes the ability of the chemokine to mediate its signal. Non-neutralizing antibodies may be useful for labeling or localization. Antibodies can be raised to various chemokine ligand or chemokine receptor proteins, including individual, polymorphic, allelic, strain, or species variants, and fragments thereof, either in their naturally occurring (full-length) forms or in their recombinant forms. Additionally, antibodies can be raised to chemokine ligands or polypeptides in either their native (or active) forms or in their inactive, e.g., denatured, forms, which may neutralize ligand capacity to mediate its signal. Antibodies may block the interaction of the ligand with its receptor, e.g., by steric hindrance, or may serve as reagents allowing labeling or localization specifically to where cognate antigen is expressed.

In particular, receptor antagonists may be produced by making antibodies which bind to the receptor and block ligand binding. With the identification of a receptor for the cytokine, antibodies to the receptor may be selected, e.g., for those which block the binding of, or signaling induced by, ligand. Or targeting reagents can be produced.

A number of immunogens may be selected to produce antibodies specifically reactive, or selective for binding, with ligand or receptor proteins. Recombinant protein is a preferred immunogen for the production of monoclonal or polyclonal antibodies. Naturally occurring protein, from appropriate sources, e.g., primate, rodent, etc., may also be used either in pure or impure form. Synthetic peptides, made using the ligand or receptor protein sequences, may also used as an immunogen for the production of antibodies. Recombinant protein can be expressed and purified in eukaryotic or prokaryotic cells as described, e.g., in Coligan, et al. (eds. 1995 and periodic supplements) *Current Protocols in Protein Science* John Wiley & Sons, New York, N.Y.; and Ausubel, et al (eds. 1987 and periodic supplements) *Current Protocols in Molecular Biology*, Greene/Wiley, New York, N.Y. Naturally folded or denatured material, perhaps expressed on cell surfaces, can be used, as appropriate, for producing antibodies. Either monoclonal or polyclonal antibodies may be generated, e.g., for subsequent use in immunoassays to measure the protein, for immunopurification methods, or for targeting methods.

Methods of producing polyclonal antibodies are well known to those of skill in the art. Typically, an immunogen, preferably a purified protein, is mixed with an adjuvant and animals are immunized with the mixture. The animal's immune response to the immunogen preparation is monitored by taking test bleeds and determining the titer of reactivity to, e.g., the ligand or receptor, protein or polypeptide of interest. For example, when appropriately high titers of antibody to the immunogen are obtained, usually after repeated immunizations, blood is collected from the animal and antisera are prepared. Further fractionation of the antisera to enrich for antibodies reactive to the protein can be performed, if desired. See, e.g., Harlow and Lane *Antibodies, A Laboratory Manual*; or Coligan (ed.) *Current Protocols in Immunology*. Immunization can also be performed through other methods, e.g., DNA vector immunization. See, e.g., Wang, et al. (1997) *Virology* 228:278–284. Affinity purification, or absorptions, can be used to select for desired specificity of binding.

Monoclonal antibodies may be obtained by various techniques familiar to those skilled in the art. Typically, spleen cells from an animal immunized with a desired antigen are immortalized, commonly by fusion with a myeloma cell. See, Kohler and Milstein (1976) *Eur. J. Immunol.* 6:511–519. Alternative methods of immortalization include transformation with Epstein Barr Virus, oncogenes, or retroviruses, or other methods known in the art. See, e.g., Doyle, et al. (eds. 1994 and periodic supplements) *Cell and Tissue Culture: Laboratory Procedures*, John Wiley and Sons, New York, N.Y. Colonies arising from single immortalized cells are screened for production of antibodies of the desired specificity and affinity for the antigen, and yield of the monoclonal antibodies produced by such cells may be enhanced by various techniques, including injection into the peritoneal cavity of a vertebrate host. Alternatively, one may isolate DNA sequences which encode a monoclonal antibody or a binding fragment thereof by screening a DNA library from human B cells according, e.g., to the general protocol outlined by Huse, et al. (1989) *Science* 246:1275–1281.

Antibodies or binding compositions, including binding fragments and single chain versions, against predetermined fragments of receptor or ligand polypeptides can be raised by immunization of animals with conjugates of the fragments with carrier proteins as described above. Monoclonal antibodies are prepared from cells secreting the desired antibody. These antibodies can be screened for binding to normal or defective ligand protein, or screened for capacity to block cell ligand mediated flux, chemoattraction, or chemokinetic activity. These monoclonal antibodies will usually bind with at least a $K_D$ of about 1 mM, more usually at least about 300 $\mu$M, typically at least about 10 $\mu$M, more typically at least about 30 $\mu$M, preferably at least about 10 $\mu$M, and more preferably at least about 3 $\mu$M or better.

In some instances, it is desirable to prepare monoclonal antibodies (mAbs) from various mammalian hosts, such as mice, rodents, primates, humans, etc. Description of techniques for preparing such monoclonal antibodies may be found in, e.g., Stites, et al. (eds.) *Basic and Clinical Immunology* (4th ed.) Lange Medical Publications, Los Altos, Calif., and references cited therein; Harlow and Lane (1988) *Antibodies: A Laboratory Manual* CSH Press; Goding (1986) *Monoclonal Antibodies: Principles and Practice* (2d ed.) Academic Press, New York, N.Y.; and particularly in Kohler and Milstein (1975) *Nature* 256:495–497, which discusses one method of generating monoclonal antibodies. Summarized briefly, this method involves injecting an animal with an immunogen. The animal is then sacrificed and cells taken from its spleen, which are then fused with myeloma cells. The result is a hybrid cell or "hybridoma" that is capable of reproducing in vitro. The population of hybridomas is then screened to isolate individual clones, each of which secrete a single antibody species to the immunogen. In this manner, the individual antibody species obtained are the products of immortalized and cloned single B cells from the immune animal generated in response to a specific site recognized on the immunogenic substance.

Other suitable techniques involve selection of libraries of antibodies in phage or similar vectors. See, e.g., Huse, et al. (1989) "Generation of a Large Combinatorial Library of the Immunoglobulin Repertoire in Phage Lambda," *Science* 246:1275–1281; and Ward, et al. (1989) *Nature* 341:544–546. The polypeptides and antibodies of the present invention may be used with or without modification, including chimeric or humanized antibodies. Frequently, the polypeptides and antibodies will be labeled by joining, either covalently or non-covalently, a substance which provides for a detectable signal. A wide variety of labels and conjugation techniques are known and are reported extensively in both the scientific and patent literature. Suitable labels include radionuclides, enzymes, substrates, cofactors, inhibitors, fluorescent moieties, chemiluminescent moieties, magnetic particles, and the like. Patents teaching the use of such labels include U.S. Pat. Nos. 3,817,837; 3,850,752; 3,939,350; 3,996,345; 4,277,437; 4,275,149; and 4,366,241. Also, recombinant immunoglobulins may be produced, see, Cabilly, U.S. Pat. No. 4,816,567; and Queen, et al. (1989) *Proc. Nat'l Acad. Sci. USA* 86:10029–10033; or made in transgenic mice, see Mendez, et al. (1997) *Nature Genetics* 15:146–156.

Antibody binding compounds, including binding fragments, of this invention can have significant diagnostic or therapeutic value. They can be useful as non-neutralizing binding compounds and can be coupled to toxins or radionuclides so that when the binding compound binds to the antigen, a cell expressing it, e.g., on its surface, is killed. Further, these binding compounds can be conjugated to drugs or other therapeutic agents, either directly or indirectly by means of a linker, and may effect drug targeting.

C. Other Molecules

Antibodies are merely one form of specific binding compositions. Other binding compositions, which will often have similar uses, include molecules that bind with specificity to the receptor, e.g., CCR7, CXCR4, or GPR2, in a binding partner-binding partner fashion, an antibody-antigen interaction, a ligand:receptor interaction with or without signaling, or in a natural physiologically relevant protein-protein interaction, either covalent or non-covalent, e.g., proteins which specifically associate with chemokine receptor protein. The molecule may be a polymer, or chemical reagent. A functional analog may be a protein with structural modifications, or may be a structurally unrelated molecule, e.g., which has a molecular shape which interacts with the appropriate binding determinants. Application of, e.g., Systematic Evolution of Ligand by Exponential Enrichment (SELEX) technology, methods are available to select specific binding constructs for desired targets. See, e.g., Colas, et al. (1996) *Nature* 380:548–550; Cohen, et al. (1998) *Proc. Nat'l Acad. Sci. USA* 95:14272–14277; Kolonin, et al. (1998) *Proc. Nat'l Acad. Sci. USA* 95:14266–14271; Famulok, et al. (1998) *Curr. Opin. Chem. Biol.* 2:320–327; and Eaton, et al. (1997) *Bioorg. Med. Chem.* 5:1087–1096.

Drug screening can be performed to identify compounds having capacity to bind to receptor, and/or to block chemoattraction to chemokine, Ca++flux, or the natural interaction with ligand. Subsequent biological assays can then be utilized to determine if the compound has intrinsic binding or blocking activity, e.g., an antagonist. Pertussis toxin is one compound known to block certain functions of the chemokine receptor signaling in a manner distinct from the ligand/receptor interaction. Mutein antagonists may be developed which maintain receptor binding but lack signaling.

Structural studies of the ligands will lead to design of new variants, particularly analogs exhibiting antagonist properties on the receptor. This can be combined with previously described screening methods to isolate muteins exhibiting desired spectra of activities. Or ligands may be used to target or label receptor bearing cells, e.g., primary tumors.

As receptor specific binding molecules are provided, also included are small molecules identified by screening procedures. In particular, it is well known in the art how to screen for small molecules which interfere, e.g., with ligand binding to the receptor, often by specific binding to the receptor and blocking of binding by natural ligand. See, e.g., meetings on High Throughput Screening, International Business Communications, Southborough, Mass. 01772-1749. Such molecules may compete with natural ligands, and selectively bind to the respective chemokines or CCR7, CXCR4, or GPR2 receptors. Similarly, assays may be developed which can screen for blockage of downstream signaling pathways of the chemokine signaling pathways.

III. Immunoassays

Immunoassays are valuable in diagnosing those cancers which will be responsive or non-responsive to treatments, as described. Qualitative or quantitative measurement of a particular protein can be performed by a variety of immunoassay methods. For a review of immunological and immunoassay procedures in general, see Stites and Terr (eds. 1991) *Basic and Clinical Immunology* (7th ed.). Moreover, the immunoassays of the present invention can be performed in many configurations, which are reviewed extensively in, e.g., Maggio (ed. 1980) *Enzyme Immunoassay* CRC Press, Boca Raton, Fla.; Tijan (1985) "Practice and Theory of Enzyme Immunoassays," *Laboratory Techniques in Biochemistry, and Molecular Biology*, Elsevier Science Publishers B.V., Amsterdam; Harlow and Lane *Antibodies: A Laboratory Manual*, supra; Chan (ed. 1987) *Immunoassay: A Practical Guide* Academic Press, Orlando, Fla.; Price and Newman (eds. 1991) *Principles and Practice of Immunoassays* Stockton Press, NY; and Ngo (ed. 1988) *Non-isotopic Immunoassays* Plenum Press, NY.

In particular, the present invention provides various primary or metastatic cancers susceptible to analysis or diagnosis by evaluating expression of select chemokine receptors. For example, the likelihood of metastasis would be evaluated by the numbers or types of cells expressing these chemokine receptors, making the cell susceptible to chemoattraction by the matching ligand. Prophylactic treatment may be useful to prevent the recruitment of such tumors to remote metastatic targets, or to label specifically those targets while still small. Alternatively, early targeting of primary tumors may be effected with the labeling reagents.

Immunoassays for measurement of receptor proteins or peptides can be performed by a variety of methods known to those skilled in the art. In brief, immunoassays to measure the protein can be either competitive or noncompetitive binding assays. In competitive binding assays, the sample to be analyzed competes with a labeled analyte for specific binding sites on a capture agent bound to a solid surface. Preferably the capture agent is an antibody specifically reactive with receptor proteins produced as described above. The concentration of labeled analyte bound to the capture agent is inversely proportional to the amount of free analyte present in the sample.

In a competitive binding immunoassay, typically the receptor protein present in the sample competes with labeled protein for binding to a specific binding agent, e.g., an antibody specifically reactive with the receptor protein. The binding agent may be bound to a solid substrate or surface to effect separation of bound labeled protein from the unbound labeled protein. Alternately, the competitive binding assay may be conducted in liquid phase and a variety of techniques known in the art may be used to separate the bound labeled protein from the unbound labeled protein. Following separation, the amount of bound labeled protein is determined. The amount of protein present in the sample is inversely proportional to the amount of labeled protein binding.

Alternatively, a homogeneous immunoassay may be performed in which a separation step is not needed. In these immunoassays, the label on the protein is altered by the binding of the protein to its specific binding agent. This alteration in the labeled protein results in a decrease or increase in the signal emitted by label, so that measurement of the label at the end of the immunoassay allows for detection or quantitation of the protein.

Diagnostic detection of receptor proteins may also be performed by a variety of noncompetitive immunoassay methods. For example, a two-site, solid phase sandwich immunoassay may be used. In this type of assay, a binding agent for the protein, e.g., an antibody, is attached to a solid support. A second protein binding agent, which may also be an antibody, and which binds the protein at a different site, is labeled. After binding at both sites on the protein has occurred, the unbound labeled binding agent is removed and the amount of labeled binding agent bound to the solid phase is measured. The amount of labeled binding agent bound is directly proportional to the amount of protein in the sample.

Western blot analysis can be used to determine the presence of receptor proteins in a sample. Electrophoresis is carried out, e.g., on a tissue sample suspected of containing the protein. Following electrophoresis to separate the proteins, and transfer of the proteins to a suitable solid support, e.g., a nitrocellulose filter, the solid support is incubated with an antibody reactive with the protein. This antibody may be labeled, or alternatively may be detected by subsequent incubation with a second labeled antibody that binds the primary antibody.

The immunoassay formats described above may employ labeled assay components. The label may be coupled directly or indirectly to the desired component of the assay according to methods well known in the art. A wide variety of labels and methods may be used. Traditionally, a radioactive label incorporating $3_H$, $125_I$, $35_S$, $14_C$, or $32_P$ was used. Non-radioactive labels include ligands which bind to labeled antibodies, fluorophores, chemiluminescent agents, enzymes, and antibodies which can serve as specific binding pair members for a labeled ligand. The choice of label depends on sensitivity required, ease of conjugation with the compound, stability requirements, and available instrumentation. For a review of various labeling or signal producing systems which may be used, see U.S. Pat. No. 4,391,904.

Antibodies reactive with a particular protein can also be measured by a variety of immunoassay methods. Thus modifications of the above procedures may be used to determine the amounts or affinities of various ligand analogs or ligand or receptor antibody preparations. For a review of immunological and immunoassay procedures applicable to the measurement of antibodies by immunoassay techniques, see, e.g., Stites and. Terr (eds.) *Basic and Clinical Immunology* (7th ed.) supra; Maggio (ed.) *Enzyme Immunoassay*, supra; and Harlow and Lane *Antibodies, A Laboratory Manual*, supra.

Screens to evaluate the binding and activity of mAbs and binding compositions encompass a variety of methods. Binding can be assayed by detectably labeling the antibody or binding composition as described above. Cells responsive to ligand can be used to assay antibody or binding composition.

To evaluate ligand chemoattraction or chemokinetic ability, experimental animals, e.g., mice, are preferably used. Cell counts are made prior to and at various time points after administration of a bolus of the candidate agonist or antagonist. Levels are analyzed in various samples, e.g., blood, serum, nasal or pulmonary lavages, or tissue biopsy staining. A successful depleting mAb or binding composition will, e.g., significantly lower the level of chemoattraction of receptor bearing cells. Such may be at least about 10%, preferably at least about 20%, 30%, 50%, 70%, or more.

Evaluation of antibodies can be performed in other animals, e.g., humans using various methods. For example, blood samples are withdrawn from patients suffering from a potential metastatic disease or disorder before and after treatment with a candidate mAb.

IV. Uses

The tissue-selective homing of metastatic tumors has long been recognized. Recent advances in the field support a model in which cell homing is achieved by sequential engagement of differentially expressed and independently regulated vascular and leukocyte adhesion molecules, and signaling receptors and their ligands. Butcher and Picker (1996) *Science* 272:60–66. The observation that chemokines, a superfamily of small secreted proteins with G protein-coupled receptors (Baggiolini (1998) *Nature* 392:565–568) can attract leukocytes led to the hypothesis that chemokines provide key signals directing recruitment of T lymphocyte subsets into lymphoid and extra-lymphoid immune effector sites. Analogously, tumor metastasis appears to make use of many similar processes, which may be similarly blocked.

A statistically significant change in the numbers of primary tumor or metastasizing cells will typically be at least about 10%, preferably 20%, 30%, 50%, 70%, 90%, or more. The effects may be specific in blocking tumor growth or progression or chemoattraction to specific points, or may be chemokinetic, in reducing general movement of cells, but not necessarily in a specific direction, e.g., of concentration gradient.

The present invention will be useful in the treatment of medical conditions or diseases associated with cancers. See, e.g., Bertino, et al. (eds. 1996) *Encyclopedia of Cancer* Academic Press; Devita, et al. (eds. 1997) *Cancer: Principles & Practice of Oncology* Lippincott, Williams and Wilkins; Devita (1997) *Principles and Practice of Oncology* Lippincott Williams and Wilkins; Cavalli, et al. (1996) *Textbook of Medical Oncology* Dunitz Martin Ltd; Horwich (ed. 1995) *Oncology: A Multidisciplinary Textbook* Lippincott-Raven; Peckham, et al. (eds. 1995) *Oxford Textbook of Oncology* Oxford Univ. Press; Mendelsohn, et al. (1995) *The Molecular Basis of Cancer* Saunders, Philadelphia; and McArdle (1990) *Surgical Oncology: Current Concepts and Practice* Butterworth-Heinemann. The specific reagents and antagonists described may be combined with other treatments of the medical conditions described herein, e.g., a chemotherapy, radiation therapy, immunotherapy, or surgical method, including alkylating agents, antimetabolites, antihormones, therapeutic for various symptoms, e.g., painkillers, diuretics, antidiuretics, antivirals, antibiotics, nutritional supplements, anemia therapeutics, blood clotting therapeutics, bone therapeutics, and psychiatric and psychological therapeutics.

To prepare pharmaceutical or sterile compositions including, e.g., the desired antagonist, the material is admixed with a pharmaceutically acceptable carrier or excipient which is preferably inert. Preparation of such pharmaceutical compositions is known in the art, see, e.g., *Remington's Pharmaceutical Sciences* and *U.S. Pharmacopeia: National Formulary*, Mack Publishing Company, Easton, Pa. (1984). Typically, therapeutic compositions are sterile.

Specific labeling reagents or antagonists, e.g., ligand muteins, antibodies, or binding compositions, are normally administered parenterally, preferably intravenously. Since such protein or peptide antagonists may be immunogenic they are preferably administered slowly, either by a conventional IV administration set or from a subcutaneous depot, e.g. as taught by Tomasi, et al., U.S. Pat. No. 4,732,863. Small molecule drugs may be orally active, or administered in other standard methods.

When administered parenterally the therapeutics will typically be formulated in a unit dosage injectable form (solution, suspension, emulsion) in association with a pharmaceutically acceptable parenteral vehicle. Such vehicles are inherently non-toxic and non-therapeutic. The antagonist may be administered in aqueous vehicles such as water, saline, or buffered vehicles with or without various additives and/or diluting agents. Alternatively, a suspension, such as a zinc suspension, can be prepared to include the peptide. Such a suspension can be useful for subcutaneous (SQ), intradermal (ID), or intramuscular (IM) injection. The proportion of therapeutic entity and additive can be varied over a broad range so long as both are present in effective amounts. The therapeutic is preferably formulated in purified form substantially free of aggregates, other proteins, endotoxins, and the like, at concentrations of about 5 to 30 mg/ml, preferably 10 to 20 mg/ml. Preferably, the endotoxin levels are less than 2.5 EU/ml. See, e.g., Avis, et al. (eds. 1993) *Pharmaceutical Dosage Forms: Parenteral Medications* 2d ed., Dekker, NY; Lieberman, et al. (eds. 1990) *Pharmaceutical Dosage Forms: Tablets* 2d ed., Dekker, NY; Lieberman, et al. (eds. 1990) *Pharmaceutical Dosage Forms: Disperse Systems* Dekker, NY; Fodor, et al. (1991) *Science* 251:767–773; Coligan (ed.) *Current Protocols in Immunology*; Hood, et al. *Immunology* Benjamin/Cummings; Paul (ed. 1997) *Fundamental Immunology* 4th ed., Academic Press; Parce, et al. (1989) *Science* 246:243–247; Owicki, et al. (1990) *Proc. Nat'l Acad. Sci. USA* 87:4007–4011; and Blundell and Johnson (1976) *Protein Crystallography*, Academic Press, New York.

Selecting an administration regimen for a therapeutic agonist or antagonist depends on several factors, including the serum or tissue turnover rate of the therapeutic, the immunogenicity of the therapeutic, the accessibility of the target cells, and the general tolerance of the patient to the stress of therapy. Preferably, an administration regimen maximizes the amount of therapeutic delivered to the patient consistent with an acceptable level of side effects. Accordingly, the amount of therapeutic delivered depends in part on the particular antagonist and the severity of the condition being treated. Guidance in selecting appropriate doses of antibodies is found in the literature on therapeutic uses, e.g. Bach et al., chapter 22, in Ferrone, et al. (eds. 1985) *Handbook of Monoclonal Antibodies* Noges Publications, Park Ridge, N.J.; and Russell, pgs. 303–357, and Smith et al., pgs. 365–389, in Haber, et al. (eds. 1977) *Antibodies in Human Diagnosis and Therapy* Raven Press, New York, N.Y.

Determination of the appropriate dose is made by the clinician, e.g., using parameters or factors known in the art to affect treatment or predicted to affect treatment. Generally, the dose begins with an amount somewhat less than the optimum dose and it is increased by small increments thereafter until the desired or optimum effect is achieved relative to any negative side effects. Numbers of receptor bearing cells in defined samples might be important indicators of when an effective dose is reached. Preferably, an antibody or binding composition thereof that will be used is derived from the same species as the animal targeted for treatment, thereby minimizing a humoral response to the reagent.

The total weekly dose ranges for antibodies or fragments thereof, which specifically bind to ligand, range generally from about 1 ng, more generally from about 10 ng, typically from about 100 ng; more typically from about 1 $\mu$g, more typically from about 10 $\mu$g, preferably from about 100 $\mu$g, and more preferably from about 1 mg per kilogram body weight. Although higher amounts may be more efficacious, the lower doses typically will have fewer adverse effects. Generally the range will be less than 100 mg, preferably less than about 50 mg, and more preferably less than about 25 mg per kilogram body weight.

The weekly dose ranges for antagonists, e.g., antibody, binding fragments, range from about 10 $\mu$g, preferably at least about 50 $\mu$g, and more preferably at least about 100 $\mu$g per kilogram of body weight. Generally, the range will be less than about 1000 $\mu$g, preferably less than about 500 $\mu$g, and more preferably less than about 100 $\mu$g per kilogram of body weight. Dosages are on a schedule which effects the desired treatment and can be periodic over shorter or longer term. In general, ranges will be from at least about 10 $\mu$g to about 50 mg, preferably about 100 $\mu$g to about 10 mg per kilogram body weight.

Other antagonists of the ligands, e.g., muteins, are also contemplated. Hourly dose ranges for muteins range from at least about 10 $\mu$g, generally at least about 50 $\mu$g, typically at least about 100 $\mu$g, and preferably at least 500 $\mu$g per hour. Generally the dosage will be less than about 100 mg, typically less than about 30 mg, preferably less than about 10 mg, and more preferably less than about 6 mg per hour. General ranges will be from at least about 1 $\mu$g to about 1000 $\mu$g, preferably about 10 $\mu$g to about 500 $\mu$g per hour.

The phrase "effective amount" means an amount sufficient to effect a desired response, or to ameliorate a symptom or sign, e.g., of metastasis or primary tumor progression, size, or growth. Typical mammalian hosts will include mice, rats, cats, dogs, and primates, including humans. An effective amount for a particular patient may vary depending on factors such as the condition being treated, the overall health of the patient, the method, route, and dose of administration and the severity of side affects. Preferably, the effect will result in a change in quantitation of at least about 10%, preferably at least 20%, 30%, 50%, 70%, or even 90% or more. When in combination, an effective amount is in ratio to a combination of components and the effect is not limited to individual components alone.

An effective amount of therapeutic will modulate the symptoms typically by at least about 10%; usually by at least about 20%; preferably at least about 30%; or more preferably at least about 50%. Alternatively, modulation of migration will mean that the migration or trafficking of various cell types is affected. Such will result in, e.g., statistically significant and quantifiable changes in the numbers of cells being affected. This may be a decrease in the numbers of target cells being attracted within a time period or target area. Rate of primary tumor progression, size, or growth may also be monitored.

The present invention provides reagents which will find use in therapeutic applications as described elsewhere herein, e.g., in the general description for treating neoplastic disorders. See, e.g., Berkow (ed.) *The Merck Manual of Diagnosis and Therapy*, Merck & Co., Rahway, N.J.; Thorn, et al. *Harrison's Principles of Internal Medicine*, McGraw-Hill, N.Y.; Gilman, et al. (eds. 1990) *Goodman and Gilman's: The Pharmacological Bases of Therapeutics*, 8th Ed., Pergamon Press; *Remington's Pharmaceutical Sciences*, 17th ed. (1990), Mack Publishing Co., Easton, Pa.; Langer (1990) *Science* 249:1527–1533; and *Merck Index*, Merck & Co., Rahway, N.J.

Moreover, antisense nucleic acids may be used. For example, antisense polynucleotides against the ligand encoding nucleic acids may function in a manner like ligand antagonists, and antisense against the receptor may function like receptor antagonists. Thus, it may be possible to block the signaling through the pathway with antisense nucleic acids. Conversely, nucleic acids for the receptor may serve as agonists, increasing the numbers of receptor on the cell, thereby increasing cell sensitivity to ligand.

Other methods based upon these observations may be developed. The attraction may be effected to specific sites where treatment may be more effective. Gradients may be set up to attract the metastatic cells to sites of effective treatment, or to trap metastatic cells for easy removal. Conversely, receptor desensitization might be effected by flooding the system with huge excesses of the cognate ligands in defined temporal patterns. Receptor targeting may allow for specific administration of therapeutic drugs, e.g., by localized attraction, activation, absorption, or activation of killing, etc.

The broad scope of this invention is best understood with reference to the following examples, which are not intended to limit the inventions to the specific embodiments.

EXAMPLES

I. General Methods

Some of the standard methods are described or referenced, e.g., in Maniatis, et al. (1982) *Molecular Cloning, A Laboratory Manual*, Cold Spring Harbor Laboratory, Cold Spring Harbor Press; Sambrook, et al. (1989) *Molecular Cloning: A Laboratory Manual*, (2d ed.), vols. 1–3, CSH Press, NY; Ausubel, et al., *Biology*, Greene Publishing Associates, Brooklyn, N.Y.; or Ausubel, et al. (1987 and Supplements) *Current Protocols in Molecular Biology*, Greene/Wiley, New York; Innis, et al. (eds.)(1990) *PCR Protocols: A Guide to Methods and Applications* Academic Press, N.Y. Methods for protein purification include such methods as ammonium sulfate precipitation, column chromatography, electrophoresis, centrifugation, crystallization, and others. See, e.g., Ausubel, et al. (1987 and periodic supplements); Deutscher (1990) "Guide to Protein Purification" in *Methods in Enzymology*, vol. 182, and other volumes in this series; manufacturer's literature on use of protein purification products, e.g., Pharmacia, Piscataway, N.J., or Bio-Rad, Richmond, Calif.; and Coligan, et al. (eds.) (1995 and periodic supplements) *Current Protocols in Protein Science*, John Wiley & Sons, New York, N.Y. Combination with recombinant techniques allow fusion to appropriate segments, e.g., to a FLAG sequence or an equivalent which can be fused via a protease-removable sequence. See, e.g., Hochuli (1989) *Chemische Industrie* 12:69–70; Hochuli (1990) "Purification of Recombinant Proteins with Metal Chelate Absorbent" in Setlow (ed.) *Genetic Engineering, Principle and Methods* 12:87–98, Plenum Press, N.Y.; and Crowe, et al. (1992) *OIAexpress: The High Level Expression & Protein Purification System* QIAGEN, Inc., Chatsworth, Calif.

Standard immunological techniques are described, e.g., in Hertzenberg, et al. (eds. 1996) *Weir's Handbook of Experimental Immunology* vols. 1–4, Blackwell Science; Coligan (1991) *Current Protocols in Immunology* Wiley/Greene, NY; and *Methods in Enzymology* volumes. 70, 73, 74, 84, 92, 93, 108, 116, 121, 132, 150, 162, and 163.

Cell migration assays are performed as previously described, e.g., in Bacon, et al. (1988) *Br. J. Pharmacol.* 95:966–974. Other trafficking assays are also available. See, e.g., Quidling-Järbrink, et al. (1995) *Eur. J. Immunol.* 25:322–327; Koch, et al. (1994) *J. Clinical Investigation* 93:921–928; and Antony, et al. (1993) *J. Immunol.* 151: 7216–7223.

Alternatively, an activation assay or attraction assay is used. An appropriate cell type is selected, e.g., hematopoietic cells, myeloid (macrophages, neutrophils, polymorphonuclear cells, etc.) or lymphoid (T cell, B cell, or NK cells), neural cells (neurons, neuroglia, oligodendrocytes, astrocytes, etc.), or stem cells, e.g., progenitor cells which differentiate to other cell types, e.g., gut crypt cells and undifferentiated cell types.

Chemokines may also be assayed for activity in hemopoietic assays as described, e.g., by H. Broxmeyer. See Bellido, et al. (1995) *J. Clinical Investigation* 95:2886–2895; and Jilka, et al. (1995) *Expt'l Hematology* 23:500–506. They may be assayed for angiogenic activities as described, e.g., by Streiter, et al. (1992) *Am. J. Pathol.* 141:1279–1284. Or for a role in inflammation. See, e.g., Wakefield, et al. (1996) *J. Surgical Res.* 64:26–31.

Other assays will include those which have been demonstrated with other chemokines. See, e.g., Schall and Bacon (1994) *Current Opinion in Immunology* 6:865–873; and Bacon and Schall (1996) *Int. Arch. Allergy & Immunol.* 109:97–109. Ca2+ flux upon chemokine stimulation is measured according to the published procedure described in Bacon, et al. (1995) *J. Immunol.* 154:3654–3666.

FACS analyses are described in Melamed, et al. (1990) *Flow Cytometry and Sorting* Wiley-Liss, Inc., New York, N.Y.; Shapiro (1988) *Practical Flow Cytometry* Liss, New York, N.Y.; and Robinson, et al. (1993) *Handbook of Flow Cytometry Methods* Wiley-Liss, New York, N.Y.

II. Cell Culture and Tissue Samples

Human primary cells were obtained, e.g., from the ATCC and clinical collaborators. Additional cell cultures and tumor samples are collected. Clinical sources are available, e.g., Cooperative Human Tissue Network, NIH.

Panels of breast cancer, head and neck, and melanoma cell lines were collected. Additional target primary cell lines to be collected include, e.g., prostate cancer, gastrointestinal cancer, and lung cancer cell lines.

Tissue samples are also collected from primary tumors. Primate, e.g., human, are preferred, but in many circumstances, mouse or other species may be collected. Metastatic tumors will also be evaluated, both for receptor expression, and for chemokine chemoattraction assays. Additional tumors to be evaluated include, e.g., prostate, gastrointestinal, and lung cancers.

Also, chemokine expression will be evaluated for lymph node, bone marrow, brain, liver, skin, and lung. Those chemokines which are expressed therefrom are candidate chemoattractants for cancers which metastasize to those organs. Antagonists of the ligand and receptor should be tested for blockage of metastasis to those organs.

III. Isolation of Encoding Sequences

Human, mouse, or rat chemokine receptor or chemokine sequences are readily available. See, e.g., GenBank and Derwent patent sequence databases. Appropriate PCR primers or hybridization probes can be selected. Sequences will be useful for evaluation of expression of receptors in tumor cells or chemokines in target organs. Isolated ligand sequences will serve as starting points for mutagenesis efforts to identify mutein antagonists. Gene sequences may be useful to produce recombinant protein for antibody production.

IV. Distribution Analysis

For Southern blotting, 5 µg of each cDNA library is digested with the appropriate restriction enzymes to release the insert, subjected to gel electrophoresis, and transferred to Hybond-N$^+$ membrane. For Northern blotting, RNAs are isolated using RNAzol B (TEL-TEST, Inc.) and analyzed by electrophoresis on a 1% formaldehyde-agarose gel and transferred to Hybond-N$^+$ membrane. Northern and Southern blots are hybridized, e.g., for 16 hr at 65° C. with $^{32}$P-labeled probes obtained by randomly priming (Prime-it; Stratagene) the full length inserts. After hybridization, blots are washed at high stringency and exposed to film.

PCR methods have been applied, and chemokine or receptor specific primers may be designed. Diagnostic methods are well known. Quantitative techniques are also available, e.g., TAQMAN™. Putative metastatic tumor cells will be evaluated for expression of chemokine receptors, which may mediate metastatic attraction to specific target organs. Conversely, target organs to which metastasis is common may express chemokines which serve to chemoattract metastatic cells to them. Thus, evaluation of the chemokine production patterns by target organs may explain the tumors which are chemoattracted to establish in the secondary site.

Diagnosis of receptor expression by a primary tumor may provide guidance as to what tumors may be susceptible to blockage of metastasis by which antagonists. This may be useful in determining therapeutic treatment strategies, e.g., what tumors may be effectively treated for metastatic blockage. Moreover, specific expression of particular receptors may serve as markers for targeting therapeutic reagents to the different tumor types.

Nucleic acid expression analysis, e.g., PCR, Taqman, hybridization data, and/or RNA protection, is preferably confirmed by evaluating protein expression. This may be in the form of protein assay, e.g., Western protein blotting techniques, immunoassay, or immunohistochemistry. Statistical analysis will be useful in determining the likelihood of efficacy of antagonist treatment.

Additional confirmatory methods include, e.g., migration and invasion assays, F-actin polymerization assays, and cell motility evaluation. Transfection models may be applied to confer trafficking of otherwise inert cell types. Studies may be based upon rodent models, etc.

V. Chemoattraction Assays

Recombinant chemokine is produced, e.g., in *E. coli* and purified. See Hedrick, et al. (1998) *Blood* 91:4242–4247. A modified Boyden chamber is used. Human tumor cells, e.g., lines or primary or secondary tumors, in DMEM, pH 6.9, 0.1 bovine serum albumin, are added to the top chamber of 8 μm pore polycarbonate Transwell culture insert (Costar) and incubated with the indicated concentrations of purified chemokine in the bottom chamber for 6–24 h. The number of migrating cells of each subtype is determined, e.g., by staining and counting. See, e.g., Youngs, et al. (1997) *Int. J. Cancer* 71:257–266.

Chemotaxis assays are performed with, e.g., human tumor cells. Cell lines or primary tumor cells will be evaluated from breast; head and neck, melanoma, prostate, gastrointestinal, and lung cancers. Other cell types express the various chemokine receptors. Recombinant chemokine should have effects on the cell types expressing receptor.

VI. Antibody Production

Appropriate mammals are immunized with appropriate amounts, e.g., of chemokine gene transfected cells, e.g., intraperitoneally every 2 weeks for 8 weeks. Similar methods may be used to produce antibodies which bind to receptor, e.g., CCR7, CXCR4, or GPR2, polypeptides, or transfected cells expressing the receptor may be used. Typically, rodents are used, though other species should accommodate production of selective and specific antibodies. The final immunization is given intravenously (IV) through the tail vein.

Generic polyclonal antibodies may be collected. Alternatively, monoclonal antibodies can be produced. For example, four days after the IV injection, the spleen is removed and fused to SP2/0 and NS1 cells. HAT resistant hybridomas are selected, e.g., using a protocol designed by Stem Cell Technologies (Vancouver, BC). After 10 days of HAT selection, resistant foci are transferred to 96 well plates and expanded for 3 days. Antibody containing supernatants are analyzed, e.g., by FACS for binding to NIH3T3/surface MIP-3β transfectants. Many different MIP-3β mAbs are typically produced. Those antibodies may be isolated and modified, e.g., by labeling or other means as is standard in the art. See, e.g., Harlow and Lane (1988) *Antibodies: A Laboratory Manual* CSH Press; Goding (1986) *Monoclonal Antibodies: Principles and Practice* (2d ed.) Academic Press, New York, N.Y. Methods to conjugate magnetic reagents, toxic entities, labels, attach the antibodies to solid substrates, to sterile filter, etc., are known in the art.

VII. Purification of Cells

Chemokine responsive cells may be identified using the reagents described herein. For example, cells which are chemoattracted towards, e.g., SDF-1 may be purified from other cells by collecting those cells which traverse towards SDF-1. Such chemotaxis may be to a source of chemokine, or may be across a porous membrane or other substrate. See above, in the microchemotaxis assay.

Alternatively, responsive cells may be identified by expression of the receptor, e.g., CXCR4, as provided herein. Thus, antibodies which recognize CXCR4 may be used as a positive marker for sorting cells likely to respond to SDF-1, and thus be chemoattracted to bone marrow. Conversely, the marker may be used to deplete CXCR4 bearing cells, e.g., by magnetic depletion or toxic conjugates.

Analysis of human samples can be evaluated in a similar manner. A biological sample, e.g., blood, tissue biopsy sample, lung or nasal lavage, skin punch, is obtained from an individual suffering from a neoplastic related disorder. Chemokine responsive cell analysis is performed, e.g., by FACS analysis, or similar means. And those cells may be primary tumor cells which are to be targeted, e.g., by toxic conjugates.

VIII. Chemokine Antagonists

Various antagonists of designated chemokines are made available. For example, antibodies against the chemokine itself may block the binding of ligand to its receptor, thereby serving as a direct receptor antagonist. Other antagonists may function by blocking the binding of ligand to receptor, e.g., by binding to the receptor in a way to preclude the possibility of binding of ligand. Other antagonists, e.g., mutein antagonists or aptamers, may bind to the receptor without signaling, thereby blocking a true agonist from binding. Many of these may serve to block the signal transmitted to target cells, e.g., specifically SDF-1-responsive cells. Small molecule compounds may also be identified which block interaction of ligand with receptor.

Information on the criticality of particular residues is determined, e.g., using standard procedures and analysis. Standard mutagenesis analysis is performed, e.g., by generating many different variants at determined positions, e.g., at the positions likely involved in receptor binding, and evaluating biological activities of the variants. This may be performed to the extent of determining positions which modify activity, or to focus on specific positions to determine the residues which can be substituted to either retain, block, or modulate biological activity.

Alternatively, analysis of natural variants can indicate what positions tolerate natural mutations. This may result from populational analysis of variation among individuals, or across strains or species. Samples from selected individuals are analyzed, e.g., by PCR analysis and sequencing. This allows evaluation of population polymorphisms.

IX. Labeling of Cells

With specific antibodies, not necessarily functionally blocking, labeling of cells may be performed. Antibodies of appropriate specificity can, e.g., be labeled with a detectable signal. Fluorescent antibodies are a common example.

Certain cells may be labeled in solution, e.g., individual cells expressing surface antigens. FACs sorting is based mostly on this property. Other cells may be labeled in tissue form, e.g., immunohistochemistry. The means to get antibody into fixed tissues are known, and similar methods may be used in unfixed tissues, ex vivo, or in vivo. See, e.g., Young and Heath (eds. 2000) *Wheater's Functional Histology: A Text and Colour Atlas* (Book with CD-ROM) Churchill Livingstone; Kerr (1999) *Atlas of Functional Histology* Mosby; and Ross, et al. (eds. 1995) *Histology: A Text and Atlas* Lippincott, Williams & Wilkins.

In situ cellular labeling of primary or secondary tumors by antibody may be used to induce natural killing mechanisms, e.g., antigen dependent cell-mediated cytotoxicity (ADCC), complement mediated cell lytic processes, or opsinization and macrophage phagocytosis, among others. Specific localization of the receptor markers with antibodies may be useful in both diagnostic and therapeutic contexts. Diagnostically, the antibodies may allow localization of receptor expressing primary tumor cells, e.g., by use of radio-opaque labels, to determine the location and extent of tumor growth or metastasis. The antibodies may be used to localize an activating agent, e.g., as alkaline phosphatase is localized and acts on substrate, similar to that mechanism used for immunohistochemistry applications. A similar strategy may be used to locally enzymatically activate a killing process, e.g., to activate an otherwise inert toxin. For example, an inactive lectin (pro-lectin) may become proteolytically activated by an antibody enzyme conjugate. Or, an energy absorbing reagent may be conjugated to the antibody, thereby specifically localizing the reagent which absorbs energy to cause tissue in proximity to become subject to concentration of an external radiation source.

All citations herein are incorporated herein by reference to the same extent as if each individual publication or patent application was specifically and individually indicated to be incorporated by reference.

Many modifications and variations of this invention can be made without departing from its spirit and scope, as will be apparent to those skilled in the art. The specific embodiments described herein are offered by way of example only, and the invention is to be limited by the terms of the appended claims, along with the full scope of equivalents to which such claims are entitled; and the invention is not to be limited by the specific embodiments that have been presented herein by way of example.

What is claimed is:

1. A method for reducing metastasis of a carcinoma cell in a subject comprising administering an anti-SDF-1 antibody or an anti-CXCR4 antibody or binding fragment thereof to the subject wherein the carcinoma cell is selected from the group consisting of a breast cell, a melanoma cell, and a prostate cell.

2. The method of claim 1, wherein said metastasis is organ specific.

3. The method of claim 1, wherein said metastasis is to a lymph node, bone marrow, or skin.

4. The method of claim 1, wherein the subject is further administered pertussis toxin.

5. The method of claim 1, wherein the subject is further administered an other anti-cancer treatment.

6. The method of claim 5, wherein said anti-cancer treatment is administered before said antibody is administered.

7. The method of claim 5, wherein said anti-cancer treatment is chemotherapy.

8. The method of claim 5, wherein said anti-cancer treatment is radiation therapy.

9. The method of claim 5, wherein said anti-cancer treatment is immunotherapy.

10. The method of claim 5, wherein said anti-cancer treatment is surgery.

* * * * *